US006677499B2

(12) United States Patent
Crosier et al.

(10) Patent No.: US 6,677,499 B2
(45) Date of Patent: Jan. 13, 2004

(54) MODULATION OF MEMORY, LEARNING AND/OR ANXIETY STATES

(75) Inventors: Philip S. Crosier, Auckland (NZ); Kathryn E. Crosier, Auckland (NZ)

(73) Assignee: Auckland Uniservices Limited, Auckland (NZ)

( * ) Notice: Subject to any disclaimer, the term of this patent is extended or adjusted under 35 U.S.C. 154(b) by 19 days.

(21) Appl. No.: 10/121,624

(22) Filed: Apr. 15, 2002

(65) Prior Publication Data

US 2002/0111293 A1 Aug. 15, 2002

Related U.S. Application Data

(63) Continuation of application No. 09/670,619, filed on Sep. 27, 2000, now abandoned.

(51) Int. Cl.$^7$ ..................... G01N 33/00; A01K 67/027
(52) U.S. Cl. ............................................. 800/3; 800/18
(58) Field of Search ..................... 800/18, 3; 435/183

(56) References Cited

U.S. PATENT DOCUMENTS

| 5,709,858 A | 1/1998 | Godowski et al. ....... 424/143.1 |
| 5,766,863 A | 6/1998 | Godowski et al. ......... 435/7.21 |
| 5,955,420 A | 9/1999 | Chen et al. .................... 514/2 |
| 6,096,527 A | 8/2000 | Godowski et al. .......... 435/194 |

FOREIGN PATENT DOCUMENTS

| WO | 94/19463 | 9/1994 |
| WO | 97/40153 | 10/1997 |

OTHER PUBLICATIONS

Sigmund, Viewpoint: Are studies in genetically altered mice out of control?, 2000, Arterioscler Thromb. Vasc. Biol., vol. 20, pp. 1425–1429.*
Wall, Transgenic livestock: Progress and prospects for the future, 1996, Theriogenology, vol. 45, pp. 57–68.*
Mullins et al., Perspective Series: Molecular medicine in genetically engineered animals, 1996, J. Clin. Invest., vol. 97, pp. 1557–1559.*
Campbell et al., Totipotency or multipotentiality of cultured cells: Applications and progress, 1997, Theriogenology, vol. 47, pp. 63–72.*
Bradley et al., Modifying the mouse: Design and desire, 1992, Bio/Technology, vol. 10, pp. 534–539.*
Lewis et al, "Analysis of the Murine Dtk Gene Identifies Conversation . . . ," Genomics, vol. 31, pp. 13–19 (1996).
Crosier et al, "The Dtk receptor tyrosine kinase, which binds . . . ," Experimental Hematology, vol. 24, pp. 318–323 (1996).
Crosier et al, "Isolation of a Receptor Tyrosine Kinase (DTK) from . . . ," Growth Factors, vol. 11, pp. 125–136 (1994).
Crosier et al, "Isolation and Characterization of the Human DTK, " Growth Factors, vol. 11, pp. 137–144 (1994).
Drouet et al, Molecular basis of Alzheimer's diseasae, 2000, Cell Molecular Life Science , pp. 705–715.
Comings, Clinical and molecular genetics of ADHD and tourette syndrome, Abstract.
Todd, Genetics of attention deficit/hyperactivity disorder: Are we ready for molecular genetic studies?, 2000, American Journal of Medical Genetics (Neuropsychiatric Genetics), vol. 96, pp. 241–243.
Janus et al., Transgenic mouse models of Alzheimer's disease, 2000, Physiology & Behavior, vol. 73, pp. 873–886.
Rubia et al, Attention deficit/hyperactivity disorder: current findings and treatment, 2001, current opinion in psychiatry, vol. 14, pp. 309–316.

* cited by examiner

Primary Examiner—Anne-Marie Falk
Assistant Examiner—Celine Qian
(74) Attorney, Agent, or Firm—Nixon & Vanderhye (57) ABSTRACT

This invention relates to the modification of long-term potentiation (LTP), learning, memory and/or anxiety states. More particularly, it relates to methods of prophylactically or therapeutically treating LTP, learning, memory and/or anxiety disorders in a patient and to medicaments for use in such methods.

6 Claims, 7 Drawing Sheets

MODULATION OF MEMORY, LEARNING AND/OR ANXIETY STATES

This application is a Continuation of application Ser. No. 09/670,619, filed Sep. 27, 2000, now abandoned, the entire contents of which is hereby incorporated by reference in this application.

This invention relates to the modification of long-term potentiation (LTP), learning; memory and/or anxiety states. More particularly, it relates to methods of prophylactically or therapeutically treating LTP, learning, memory and/or anxiety disorders in a patient and to medicaments for use in such methods.

BACKGROUND

Long-term potentiation (LTP) is a long-sting increase in synaptic efficacy which is induced typically by high-frequency stimulation of afferent fibers (Bliss and Loma 1973). LTP, together with its converse, long-term depression (LTD), is considered an attractive candidate memory storage mechanism.

Consistent with this is an observed association between a severe impairment of LTP and impaired learning and retention of spatial task induced by a selective knockout of functional NMDA receptors in area CA1 of the hippocampus, McHugh et al (1996); Tsien et al (1996).

Impairment of LTP (and of learning/memory) is implicated in, or is the consequence of, a range of disorders. These include, for example, Alzheimer's Disease and Attention Deficiency Disorder (ADD).

It is an object of this invention to provide a new approach to the modification of the LTP, learning, memory and/or anxiety state in an individual, or at least to provide the public with a useful choice.

The Dtk receptor tyrosine kinase is a member of the Axl subfamily of receptor tyrosine kinases (RTKs) (Crosier, K. E. (1997)). The Axl subfamily currently comprises three members, Ax, Dtk and Mer. These kinases show distinct but overlapping patterns of expression in the adult mouse. with expression to varying extents in neural, reproductive, vascular and haematopoietic tissues (Faust, M. (1992); Neubauer, A. (1994), Crosier, K. E. (1994); Lai et al (1994); Crosier, P. S. (1996); Jia et al (1994); Graham et al (1994); Graham. D. K. (1995)). Dtk is primarily expressed in the adult brain and gonads, with brain expression most prominent in neurons of the cerebellum, neocortex, olfactory bulbs and the CA1 region of the hippocampus (Lai et al (1994); Schulz et al (1995)).

The applicants have now determined that Dtk has a role in hippocampal-dependent learning and memory, primarily through a signalling contribution to LTP induction and maintenance. It is this determination, together with the implications it holds for manipulating LTP and/or learning and memory, which forms the basis of this invention.

SUMMARY OF THE INVENTION

The present invention has a number of aspects.

In a first aspect, the invention provides a method of modifying the LTP, learning, memory and/or anxiety state of an individual which comprises the step of manipulating the activity of Dtk receptor tyrosine kinase in the brain of said individual.

In a further aspect, the invention provides a method of prophylactically or therapeutically treating LTP, learning, memory and/or anxiety disorders in a patient which comprises the step of increasing the activity of Dtk receptor tyrosine kinase in the brain of said patient.

In a specific embodiment, said prophylactic or therapeutic result is from maintaining a Dtk receptor tyrosine kinase initiated neuronal anti-apoptotic signal in the brain of said patient.

Preferably, the activity of Dtk receptor tyrosine kinase is increased through administering an effective amount of a stimulatory ligand. As used herein, "stimulatory ligand" means a ligand which is capable of both binding to and activating Dtk receptor tyrosine kinase signalling pathway.

In a preferred embodiment, the activity of Dtk receptor tyrosine kinase is increased through administration of the ligand Gas6 or an analog thereof.

In still a further aspect, the invention provides a method of inducing LTP, learning, memory and/or anxiety deficit(s) in an individual which comprises the step of decreasing the activity of Dtk receptor tyrosine kinase in the brain of said individual.

Conveniently, this is achieved by administering to said individual an effective amount of an inhibitory ligand. By "inhibitory ligand" it is meant any ligand which is capable of binding to the extracellular binding domain of Dtk receptor tyrosine kinase but which is incapable of activating the signalling pathway.

A decrease in the activity of Dtk receptor tyrosine kinase can also be effected through administration of the extracellular binding domain of Dtk receptor tyrosine kinase in a soluble form.

In yet a further aspect, the invention provides the use of a ligand to Dtk receptor tyrosine kinase in the preparation of a medicament for modifying the LTP, learning, memory and/or anxiety state of an individual.

Preferably, the medicament prepared effects modification of the LTP, learning, memory and/or anxiety state of an individual through manipulating the activity of Dtk receptor tyrosine kinase in the brain of said individual.

In yet a further aspect, the invention provides the use of a stimulatory ligand for Dtk receptor tyrosine kinase in the preparation of a medicament for prophylaxis or therapy of LTP, learning, memory and/or anxiety disorder(s).

In still a further aspect, the invention provides the use of a stimulatory ligand for Dtk receptor tyrosine kinase in the preparation of a medicament for inducing a neuronal anti-apoptotic signal within the brain of individual.

In yet a further aspect, the invention provides the use of the ligand Gas6 or an analog thereof in the preparation of a medicament for prophylaxis or therapy of LTP, learning, memory and/or anxiety disorder(s).

In still a further aspect, the invention provides a medicament for use in modifying the LTP, learning, memory and/or anxiety state of an individual which includes a ligand to Dtk receptor tyrosine kinase as defined above.

In still a further aspect, the invention provides a method of identifying a ligand which is capable of modifying the LTP, learning, memory and/or anxiety state of an individual which comprises the step of testing a candidate ligand for its ability to bind and activate the signalling pathway of Dtk receptor tyrosine kinase.

In yet a further aspect, the invention provides a non-human vertebrate animal, which animal normally expresses Dtk receptor tyrosine kinase in the forebrain, which has been modified genetically so that the expression of Dtk receptor tyrosine kinase is at least reduced in the forebrain.

Most preferably, the animal has been modified such that the expression of Dtk receptor tyrosine kinase is eliminated in the forebrain of the animal.

Most preferably, the animal is a mouse.

In still a further aspect, the invention provides a method of identifying a compound which is capable of enhancing LTP, learning and/or memory capability which comprises administering candidate compounds separately to a non-human animal as defined above which has a predetermined baseline LTP/learning/memory deficit and identifying those compounds which enhance LTP, learning and/or memory relative to that baseline.

In yet a further aspect, the invention provides a method of identifying a compound which is capable of reducing or ameliorating an anxiety state which comprises administering candidate compounds separately to a non-human animal as defined above which has a predetermined anxiety quotient and identifying those compounds which reduce anxiety relative to said quotient.

DESCRIPTION OF THE DRAWINGS

Although the invention is broadly as defined above, it will be appreciated by those persons skilled in the art that it is not limited thereto and that it also includes embodiments of which the following description provides examples. In particular, a better understanding of the present invention and its implications will be gained through reference to the accompanying drawings in which:

FIGS. 7A–D shows TUNEL staining in the dentate gyrus of wild-type and Dtk knockout mice. A) Wild-type B) Dtk knockout. Darkly stained TUNEL-positive cells appear mainly at the granule cell layer-hilar border (example arrowed in A).

DESCRIPTION OF THE INVENTION

The focus of the present invention is on the modification or manipulation of LTP, memory, learning and anxiety states. In particular, the invention focuses upon the role in LTP, memo, learning and/or anxiety states of an individual played by the Dtk receptor tyrosine kinase pathway.

The Dtk receptor tyrosine kinase is that referred to and described in WO 94/19463. It is a transmembrane receptor tyrosine kinase with an extracellular domain containing two immunoglobulin-like motifs followed by two fibronectin-type III repeats. This receptor tyrosine kinase is expressed in embryonic stem cells, in testis and brain tissue, particularly the forebrain and more particularly the hippocampus.

It has now been determined by the applicants that Dtk receptor tyrosine kinase is involved in LTP, learning, memory and/or anxiety states. This has been demonstrated primarily through the generation of a genetically modified non-human vertebrate animal (a mouse) which has been confirmed as a Dtk receptor tyrosine kinase null mutant by analysis at the DNA, RNA and protein level. Further, this Dtk receptor tyrosine kinase null mutant mouse has a characteristic phenotype consisting of:

(i) a defect in spatial learning and memory;
(ii) an increased anxiety-response; and
(iii) an impairment in the persistence of long-term potentiation (LTP).

The experimental section which follows details the generation of the Dtk receptor tyrosine kinase null mutant mouse and the testing performed on that mouse.

EXPERIMENTAL

Experiment 1

Development of a Dtk Receptor Tyrosine Kinase Knockout Mouse (Null Mutant)

Tissue Culture Media and Additives

D-MEM was dissolved in 95% of the final volume (1 L) of distilled water. Sodium bicarbonate (3.7 g/L) was added to the solution and the pH adjusted to 7.2 with either 10 N NaOH or concentrated HCl, respectively. The final volume was made up to 1 L with distilled water and the media sterilised by filtration through a 0.2 mM pore size cellulose acetate membrane (Millipore).

Recombinant murine Leukemia Inhibitory Factor (ESGRO) was purchased from Amrad. The approximate specific activity of mLIF was $1\times10^8$ units/mg. The mLIF was supplied at a concentration of $1\times10^6$ units/ml and was stored at 4° C. G418 sulphate (Geneticin) was purchased from GibcoBRL in powdered form. A 100 mg/ml (biological potency 687 µg/ml) stock solution was prepared in sterile, distilled water and stored at 4° C.

Fetal calf serum (FCS), horse serum and chicken serum were purchased from GibcoBRL (Auckland, New Zealand) and stored at either 4° C. or −20° C. The FCS and horse serum were heat inactivated at 56° C. for 30 minutes prior to use.

A solution of 5000 units/ml penicillin G sodium and 5000 µg/ml streptomycin sulphate in 0.85% saline was purchased from GibcoBRL and stored at 4° C.

A solution of 100×non-essential amino acids 110 mM) was purchased from GibcoBRL and stored away from light at 4° C. L-glutamine (200 mM) was purchased from GibcoBRL in powdered form. The powder was rehydrated using the appropriate volume of sterile, distilled water and stored at −20° C.

Mice

Pseudo-pregnant females used for the generation of chimeric mice were the ICR strain of mice. Chimeric mice were bred with C57BL/6J mice and their progeny intercrossed.

Preparation of Genomic DNA From Embryonic Stem Cells and Mouse Tail Biopsies Embryonic stem cells were brown on gelatin-coated 24-well plates, in the absence of feeder layers, until confluent colonies were obtained. As each well came to confluence, the medium was aspirated and the cells rinsed with PBS. The cells were incubated with 0.5 ml lysis buffer (100 mM Tris-HCl [pH 8.5], 5 mM EDTA, 0.2%, SDS [w/v] and 200 mM NaCl) at 37° C. for 16 hours. The lysates were then transferred to 1.5 ml microcentrifuge tubes containing cold 100% ethanol (1 ml) and incubated for 30–60 minutes at 4° C. on a rocking platform. The precipitated genomic DNA was then centrifuged for 15 minutes at 4° C. and the supernatant discarded. The DNA was washed with 80% ethanol (1 ml), resuspended in TE buffer (100 µl), and stored at 4° C.

Tail biopsies of no longer a 1 cm were transferred to 0.5 ml lysis buffer (100 mM Tris-HCl [pH 8.5], 5 mM EDTA, 0.2% SDS [w/v] and 200 mM NaCl) immediately upon cutting and incubated at 50° C. overnight with continuous agitation. The lysates were then shaken vigorously, transferred to 1.5 ml microcentrifuge tubes and spun for 10 minutes at room temperature. The supernatant was transferred to a fresh tube containing cold 100% ethanol (1 ml) and incubated for 30–60 minutes at 4° C. on a rocking platform. The precipitated genomic DNA was then centrifuged at 14000 rpm for 15 minutes at 4° C. and the supernatant discarded. The DNA was washed with 80% ethanol (1 ml), resuspended in TE buffer (100 µl), and stored at 4° C.

Southern Analysis

DNA samples were resolved by agarose gel electrophoresis and visualised by ultraviolet illumination. Gels containing DNA fragments larger than 10 kb were soaked in 0.25 M HCl with gentle agitation at room temperature for 10–20 minutes. The gel was then briefly rinsed in distilled water and soaked in denaturing solution (1.5 M NaCl and 0.5 M NaOH) with gentle agitation at room temperature for 30–45 minutes. The gel was rinsed again in distilled water and soaked in two changes of neutralising solution (1 M Tris-HCl [pH 7.4] and 1.5 M NaCl) with gentle agitation at room temperature for 15 minutes. The DNA was then transferred to a Hybond-N$^+$ membrane (Amersham) by capillary transfer in 20×SSC buffer for 16 hours. The membrane was briefly rinsed in 4×SSC buffer and the DNA fixed to the membrane by baking at 80° C. for 2 hours.

Pre-hybridisation was performed in 1 ml/cm$^2$ hybridisation buffer (4×SSC buffer, 5×Denhardts reagent, 100 µg/ml salmon sperm DNA and 0.5% [w/v] SDS) for at least 60 minutes at 65° C. (50° C. for oligonucleotide probes). Hybridisation was performed in fresh hybridisation buffer with $5\times10^5$ to $1\times10^6$ cpm probe/ml for 16 hours at 65° C. (50° C. for oligonucleotide probes). The membrane was then washed with a solution of 2×SSC buffer and 0.1% (w/v) SDS for 30 minutes at 65° C. This was followed by another wash in a solution of 1×SSC buffer and 0.1% (w/v) SDS for 30 minutes at 65° C. More stringent washes were performed, if necessary, to reduce non-specifically bound probe to a minimum. The membrane was then exposed to X-ray film (Kodak) in a metal cassette at −70° C. with intensifying screens.

Screening the Genomic Library

A kW251 bacterial culture (10 ml) was centrifuged at 2000 rpm (Beckman) for 10 minutes and the pellet resuspended in 10 mM MgSO$_4$ (6 ml) and SM buffer (9 ml).

An aliquot of the bacterial suspension (500 µl) was mixed with $4\times10^4$ pfu from a 129/SV bacteriophage lambda genomic library (Stratagene) and incubated at 37° C. for 15 minutes. This was then tarred with NZCYM top agarose (10 ml), prewarmed to 4° C., and poured onto NZCYM agar plates (0.132 m diameter). The plates were incubated at 37%C. for 16 hours. Duplicate plaque blots were made of each plate and the plaques screened by hybridisation to specific cDNA probes. Plaques that hybridised to the probe were removed from the plate in a plug of agar and eluted in SM buffer (1 ml) containing 2 drops chloroform (neat) for 3 hours at room temperature. The eluted phage (100 pfu) were then replated onto a NZCYM agar plate (0.082 m diameter) and duplicate plaque blots screened as described above. Plaques that hybridised to the probe were removed from the plate in a small plug of agar and eluted as described above. The eluted phage (50 pfu) were then replated onto a NZCYM agar plate (0.082 m diameter) and single plaque blots screened as described above. A single phage plaque that hybridised to the probe was removed from the plate in a small plug of agar and eluted in SM buffer (500 µl) containing 2 drops chloroform (neat).

Primary Embryonic Fibroblasts (PEFs) and Embryonic Stem (ES) Cells

Preparation of PEFs

Day 13 embryos harvested from pregnant mice that lack the interferon-γ receptor were washed twice in PBS buffer. The heads and livers were removed from the embryos using a pair of fine forceps. The bodies were rinsed in several changes of PBS buffer and then placed in a solution of trypsin-EDTA (10 embryos per 10–15 ml trypsin-EDTA). The bodies were fragmented by 3–4 passages through a 10 ml syringe and then incubated at 37° C. for 45 minutes with occasional mixing. Single cells released into the trypsin- EDTA solution were transferred to a 175 cm² culture flask containing D-MEM supplemented with 10% (v/v) FCS, 50 unite/ml penicillin, 50 µg/ml streptomycin, 2 mM L-glutamine, and $1\times10^{-4}$ M 2-b-mercaptoethanol. The remaining mixture of fragmented bodies was incubated for a further 45 minutes in 10–15 ml trypsin-EDTA, as described above. The single cells released from this incubation were transferred to a second 175 cm² culture flask containing complete growth medium. The medium was changed after the cells were incubated at 37° C. for 24 hours in a humidified atmosphere containing 10% $CO_2$. The PEFs were maintained at 37° C. in a humidified atmosphere containing 10% $CO_2$ and split 1:3 when confluent.

Preparation of Feeder Layers

The PEFs were mitotically inactivated by irradiation at a dose of 3000 rads, followed by a gentle wash in complete growth medium. The irradiated cells were then frozen and stored in liquid nitrogen. Feeder layers were prepared by thawing a vial of the irradiated cells and allowing them to attach to the surface of culture flasks or culture dishes for at least 1 hour before the addition of embryonic stem cells. The feeder layers were maintained at 37° C. in a humidified atmosphere containing 10% $CO_2$.

Maintenance of W9.5 ES Cells

W9.5 ES cells were grown in D-MEM supplemented with 15% (v/v) FCS, 50 units/ml penicillin, 50 µg/ml streptomycin, 2 mM L-glutamine, $1\times10^{-4}$ M 2-b-mercaptoethanol, $1\times10^3$ unite/ml ESGRO, 1×nucleosides solution, and 1×non-essential amino acids solution. The cells were plated at $2-5\times10^5$ cells per 25 cm² culture flask and maintained at 37° C. in a humidified atmosphere containing 10% $CO_2$. The cells were passaged every two or three days and the growth medium changed daily. Colonies were never allowed to get too large and the passage number was always kept to a minimum.

Electroporation of ES Cells

Ten 10 cm culture dishes containing feeder layers were prepared the day before electroporation. The growth medium on the ES cells was changed several hours prior to electroporation. The ES cells were harvested using a mix of trypsin-EDTA (GibcoBRL) and 1% (v/v) chicken serum (GibcoBRL). The cells were washed in complete growth medium and $2.5\times10^7$ cells resuspended in D-MEM (0.5 ml). The ES cells were then mixed gently with the linearised targeting construct (15 µg) in a 0.4 cm Gene Pulsar cuvette (Bio-Rad). The cells were incubated at room temperature for 10 minutes and then electroporated at a capacitance of 500 µF and 0.27 mV in a gene pulsar (Bio-Rad). After electroporation the cells were left for 15 minutes at room temperature, washed once with complete growth medium, and gently plated onto ten 10 cm culture dishes containing feeder layers. Selection was initiated 24 hours later by the addition of complete growth medium containing 260 µg/ml Geneticin microbiological potency of 180 µg/ml). Selection medium was changed daily and colonies picked 8 days after the initiation of selection.

Picking and Expansion of ES Cell Colonies

The day before colonies were to be picked, 24-well culture plates containing feeder layers were prepared. ES cell colonies were scored on the under-side of each 10 cm culture dish and the selection medium changed two hours prior to picking the colonies. Medium from the transfection dish was aspirated, the cells rinsed with PBS buffer and the plate gently overlayed with 2–3 ml of a mix of trypsin-EDTA (GibcoBRL) and 1% (v/v) chicken serum (GibcoBRL). Single colonies were then picked using P20 Gilson tips and each colony transferred directly into one well of a 24-well culture plate containing feeder layers. The ES cells were grown for 2–4 days with the selection medium changed daily. Each well was then split onto two new 24-well culture plates, one containing feeder layers for freezing (30% of ES cells from a single well) and one coated with gelatin for genomic DNA preparations (70% of ES cells from a single well). The ES cells on these duplicate plates were grown for 2–4 days with the selection medium changed daily.

Freezing and Thawing ES Cells in 24-well Culture Plates

Medium from each well was aspirated and the ES cells rinsed once with PBS buffer. The cells were then incubated in 2 drops of a mix of trypsin-EDTA (GibcoBRL) and 1% (v/v) chicken serum (GibcoBRL) at 37° C. for 2–4 minutes, until the colonies had detached from the surface of the plate. Complete growth medium (0.5 ml) was added to each well, the plate placed on ice for 10 minutes, and 0.5 ml of ice-cold freezing mix (20% [v/v] dimethyl sulfoxide, 20% [v/v] FCS and 60% [v/v] D-MEM) added to each well. The plate was then gently swirled, the lid sealed with tape, and the plate stored in a styrofoam box at −80° C.

To thaw, each plate was held at 37° C. for 1–2 minutes. The thawed cells were transferred into selection medium (10 ml) and spun at 1000 rpm (Beckman GS6R) for 5 minutes at room temperature. The pelleted cells were then gently resuspended in selection medium before new culture flasks or dishes containing feeder layers were seeded.

Cloning ES Cells

ES cells were plated at very low density (50–100 cells per dish) on 10 cm culture dishes containing feeder layers. After 2–3 days of growth, individual ES cell colonies were picked and expanded as described above.

Blastocyst Injections and Production of Chimeric Mice

Blastocysts were flushed from the uteri of day 4 pregnant females (strain C57BL/6J) using M2 medium. A single cell suspension of embryonic stem (ES) cells was prepared. Between 10 and 20 individual ES cells were injected into the blastocoel cavity of each blastocyst using a microinjection apparatus. The blastocysts were cultured in M16 medium and transferred to the uteri of pseudopregnant recipients (strain ICR). All manipulations were performed as described by Hogan et al (1986).

Strategy for Targeting of the Dtk Locus by Homologous Recombination

A replacement-type targeting vector (Thomas and Cappechi, 1987) was constructed to disrupt the Dtk gene by deleting exons encoding almost all of the extracellular domain of the mature receptor as well as sequences required for translation initiation and protein trafficking. The deletion encompassed approximately 10 kb of the gene and removed most of exon 3, which encodes the signal peptide region of Dtk, through to the middle of exon 11, which represents the final extracellular domain-encoding exon of the receptor. A phosphoglycerate kinase (PGK)-neomycin phosphotransferase (neo) expression cassette, containing multiple stop codons in all reading frames (Tybulewicz et al, 1991), was inserted in the deleted region in the opposite transcriptional orientation to the Dtk gene. Removal of the Dtk translation initiation codon and introduction of multiple translational stop codons upstream of sequences encoding the cytoplasmic domain of all isoforms of the receptor should generate a null mutation of the receptor.

The targeting vector contained the selectable marker flanked on either side by 893 bp of homology to the 5' end of the Dtk gene and 6.2 kb of 3⁻ homology, respectively. The 893 bp fragment was generated from the Dtk genomic subclone 117pGEM3. using restriction enzymes Acc I and Not I. This restriction fragment was blunt-ended and inserted in an antisense orientation into the blunt-ended Hind III site of a vector (pGEM-7) containing the pGK-neo expression cassette cloned into the EcoR I and Hind III sites. The 6.2 kb fragment was generated from the Dtk genomic subclone 128pGEM9.0BSa using restriction enzymes BamH I and Kpn I. This restriction fragment was subcloned into the same sites of vector pUC-BM20, excised with restriction enzymes EcoR I and EcoR V, and shuttled into the EcoR I and blunt-ended Xho I sites of the construct containing the PGK-neo expression cassette flanked by the 893 bp fragment.

Generation of Embryonic Stem Cells With a Null Allele of the Dtk Gene

The targeting construct was linearised at a unique Sal I site and electroporated into W9.5 embryonic stem (ES) cells. These cells were derived from the 129/SV strain of mouse and hence possess the agouti coat color genotype (Szabó and Mann, 1994). The ES cells were cultured on mitotically inactivated primary embryonic fibroblasts and subsequent to electroporation were maintained in growth medium containing G418. After eight days of selection, five hundred pools of G418-resistant clones were screened by Southern analysis for homologous recombinants. Genomic DNA prepared from the pools of cells was digested with the restriction enzyme Hind III and Southern blots sequentially hybridised with probes corresponding to sequences flanking the targeting vector (probe A) and the neomycin phosphotransferase gene (neo probe), respectively. Probe A was prepared from a 570 bp fragment that was excised from genomic subclone 117pGEM3.9HB with restriction enzymes Hind III and Acc I and radiolabelled by random priming. The neo probe was prepared from a 588 bp fragment excised from the pGK-neo expression cassette with the restriction enzyme Nco I and radiolabelled by random priming. The presence of a 5.6 kb Hind III restriction fragment that hybridised to probe A identified three independently derived clones (pool numbers 222, 171, and 60) teat had integrated the targeting vector by homologous recombination. The wild-type allele of the Dtk gene was observed as an 8.0 kb hybridising fragment that was of greater intensity than the fragment derived from the mutated allele, suggesting that each pool represented a mixed population of cells. Furthermore, the 5.6 kb restriction fragment also hybridised to the neo probe verifying the identity of the correctly targeted allele.

Single clones were isolated from the pools of positive cells and the genomic DNA screened by Southern analysis, as described above, to identify the clones that were homologous recombinants and contained only a single copy of the targeting vector. The presence of a 5.6⁻ kb Hind III restriction fragment that hybridised to probe A identified clones derived from pool number 222 (clone numbers 222-4 and 222-5) that had integrated the targeting vector by homologous recombination. Moreover, the 8.0 kb hybridising fragment indicative of the wild-type allele was present at an equivalent intensity indicating that these clones were homogeneous. The presence of a single hybridising fragment with the neo probe verified that clones 222-4 and 222-5 contained only one copy of the targeting vector. It is possible that these two ES cell clones are derived from the same targeting event which occurred in the original, mixed population of parent cells. The presence of a 5.6 kb Hind III restriction fragment that hybridised to probe A identified a clone derived from pool number 171 (clone number 171-23) that had integrated the targeting vector by homologous recombination. The 8.0 kb hybridising fragment derived from the wild-type allele was present at an equivalent intensity indicating that 171-23 was a pure clone, although the presence of several restriction fragments which hybridised to the neo probe demonstrated that clone 171-23 contained several randomly integrated copies of the targeting vector. The presence of a 5.6 kb Hind III restriction fragment that hybridised to probe A in every clone derived from pool number 60 illustrated that this pool of targeted cells was in fact homogeneous. However, the 8.0 kb hybridising fragment indicative of the wild-type allele was still present in every clone derived from this pool at a greater intensity than the fragment from the mutated allele, suggesting that a gene duplication event had been associated with homologous recombination of the targeting vector in these cells. Only a single 5.6 kb hybridising fragment was identified with the neo probe indicating that one copy of the targeting vector had been correctly integrated in clone 60. Interestingly, cells from clone 60 appeared to proliferate more slowly than any of the other ES cell populations.

Generation of Dtk Mutant Mice

The ES cell lines 222-4 and 222-5, which possessed a single copy of the disrupted Dtk allele, were injected into C57BL/6 blastocysts and a number of mice were generated from both ES cell clones that exhibited from 20% to 100% coat chimerism. Interestingly, many of the chimeric mice possessed square-shaped faces and developed overgrown teeth that required trimming. The severity of the phenotype appeared to be associated with the percentage of coat chimerism exhibited by the mice. The male chimeras were bred with C57BL/6J females and litters that included agouti pups obtained, indicating germline transmission of the ES cell genome. The phenotype associated with the chimeric mice was not observed in these litters of mice. Animals heterozygous for the disrupted Dtk allele were distinguished from their wild-type litter mates by Southern analysis of genomic DNA prepared from tail biopsies. The presence of a 5.6 kb Hind III restriction fragment and an 8.0 kb fragment that hybridised to probe A identified mice that possessed one mutated Dtk allele and one wild-type allele, respectively. In contrast, the presence of a single 8.0 kb Hind III restriction fragment that hybridised to probe A identified mice with two wild-type alleles of the Dtk gene. The disrupted Dtk allele was also detected in heterozygous mice by the presence of a single 5.6 kb Hind III restriction fragment that hybridised to the neo probe.

Animals heterozygous for the disrupted Dtk gene were interbred to produce litters that included homozygous offspring. The homozygous mice were distinguished from their wild-type and heterozygous litter mates by Southern analysis, as described above. The presence of a single 5.6 kb restriction fragment derived from the mutated gene and the absence of an 8.0 kb wild-type product identified homozygotes. The genotype of homozygotes was also confirmed by the presence of a single restriction fragment that hybridised to the neo probe at twice the intensity seen for products derived from heterozygotes. Homozygous mutant offspring were born from matings between heterozygous animals at a frequency that was consistent with normal Mendelian patterns of inheritance (13 [+/+], 30 [+/−], 13 [−/−]) The homozygous mutant mice were viable and appeared to be healthy. In addition, both male and female mice were fertile allowing a colony of homozygous mutant mice to be established.

Analysis of the Dtk Mutation in Mice

Examination of Dtk Transcripts in Wild-type and Dtk Mutant Mice

To facilitate characterisation of the Dtk mutation, total RNA extracted from adult brain of wild-type, heterozygous, and homozygous mutant mice were subjected to Northern analysis. The blot was hybridised with a probe corresponding to extracellular domain coding sequences of the Dtk receptor. The probe was prepared from a 715 bp restriction fragment of a previously described Dtk cDNA clone (Crosier et al, 1994) that was radiolabelled by random priming. As anticipated, the probe detected a 4.5 kb to 4.0 kb mRNA species in the wild-type mouse which was also present in the heterozygous mutant mouse. The intensity of the transcripts observed hybridising to the probe in the heterozygote appeared to be half of that seen in the wild-type, as would be expected for a mouse possessing only one copy of the wild-type allele. Furthermore, no mRNA species were detected hybridising with the extracellular domain probe in the homozygous mutant mouse, confirming that targeted disruption of the Dtk gene had removed extracellular domain coding sequences of the receptor. These findings were also corroborated by the more sensitive detection method of RT-PCR using primers that could amplify a product from the extracellular domain coding sequences of the receptor.

Since the strategy employed to disrupt the Dtk gene left the promoter regions intact, all transcripts prod-aced from the altered gene were examined by Northern analysis. A blot of total RNA extracted from adult brain of wild-type, heterozygous, and homozygous mutant mice was hybridised with a probe corresponding to cytoplasmic domain and 3' untranslated sequences of the receptor. The probe was prepared by radiolabelling antisense transcripts synthesised from a truncated cDNA clone of Dtk. As anticipated, the probe detected a 4.5 kb to 4.0 kb mRNA species in wild-type and heterozygous mutant mice at the appropriate intensity for the genotype of the mice.

To summarise: A Dtk knockout mouse has been generated by gene targeting using standard techniques. A replacement-type targeting vector (pGKneo) was constructed to disrupt the Dtk gene by deleting exons encoding almost all of the extracellular domain of the mature receptor as well as sequences required for translation initiation and protein trafficking. The deletion encompassed approximately 10 kb of the gene and removed most of exon 3, which encodes the Dtk signal peptide, through to the middle of exon 11, which encodes the final portion of the extracellular domain. The pGKneo expression cassette, which contains multiple stop codons in all reading frames was inserted in the deleted region in the opposite transcriptional orientation to the Dtk gene. The targeting vector was linearised and electroporated into W9.5 embryonic stem cells which were maintained on embryonic fibroblasts. Following drug selection, 500 pools of embryonic stem cells were screened by Southern analysis for homologous recombinants. A 5.6 kb Hind III restriction fragment identified the disrupted allele while an 8.0 kb hybridising fragment identified wild-type Dtk. In 3 pools the 5.6 kb Hind III restriction fragment was identified, demonstrating the integration of the targeting vector by homologous recombination. From these pools 2 clones were isolated, injected into C57BL/6 blastocysts and a number of mice were generated that exhibited 20 to 100% coat chimerism. The male chimeras were bred to female C57BL/6 females and litters with agouti pups were obtained indicating that germline transmission of the embryonic stem cell genome had been obtained. Heterozygous mice were identified by Southern analysis and bred to obtain homozygous offspring. Homozygous mutant offspring are born from matings between heterozygous animals at a frequency that is consistent with normal 1:2:1 ratios of Mendelian inheritance. Western blot analysis of brain lysates from targeted mice using an antibody to the Dtk C-terminus has demonstrated an absence of Dtk protein, as has immunohistochemical analysis of brain sections. The homozygous mice are viable and appear healthy.

Figure 1:
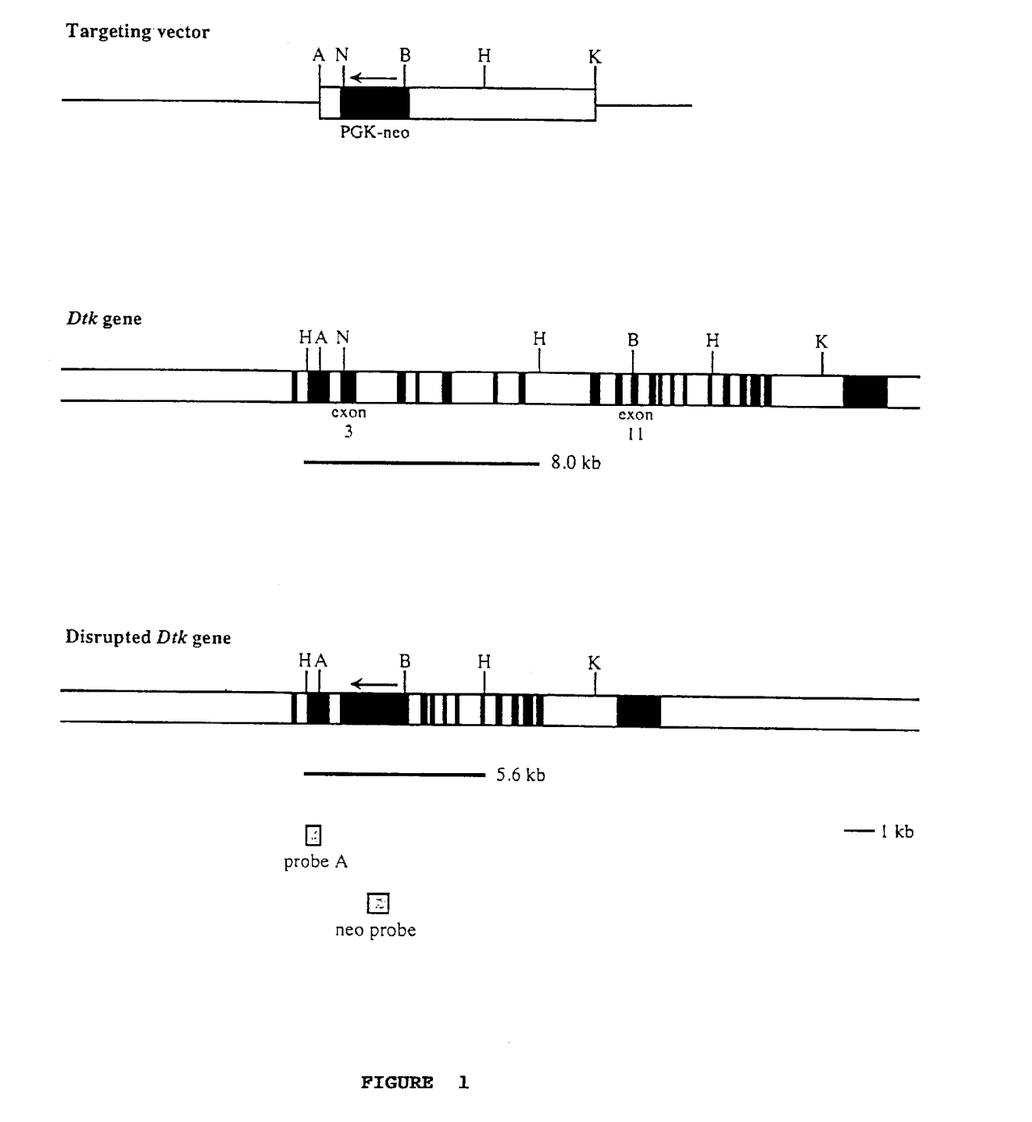
FIG. 1 shows the targeted disruption of the Dtk locus by homologous recombination. A schematic diagram of the targeting vector used for positive selection of homologous recombinants at the Dtk locus, with partial restriction map and structure of the targeted locus indicated.
Figure 2:
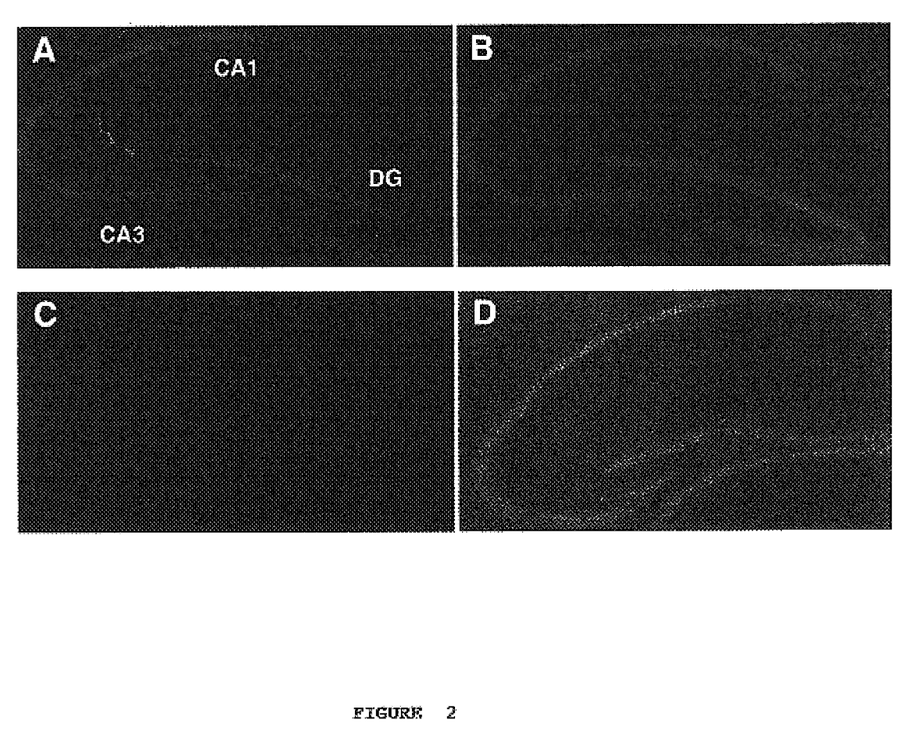
FIGS. 2A–D shows the expression of Dtk is absent in the hippocampus of Dtk knockout mice. Immunohistochemical analysis of parasaggital sections of the hippocampus from wild-Type (A and B) and Dtk knockout (C and D) mice, showing expression of Dtk (A and C) and the neuronal marker neurofilament N (Neu N, B and D) in neurons of area CA1, CA3 and the dentate gyrus (DG). Fixed sections were incubated with a mixture of a rabbit polyclonal antibody to Dtk and a mouse monoclonal antibody to Neu N (Chemicon, CA, USA). Secondary antibodies were conjugated to the fluorescent dyes CY3 (Dtk) and CY5 (Neu N). Fluorescence images were collected by laser confocal microscopy.

The targeting strategy is outlined in FIG. 1, whereas the results of analysis of the Dtk knockout mice are shown in FIG. 2.

Analysis of the Mouse

Behavioural Analysis: Barnes Circular Maze

Because Dtk is predominantly expressed in neurons of the hippocampus, an investigation has been undertaken to establish if there is all impairment of learning or memory in the Dtk knockout mice. Spatial memory, which is dependent on the functioning of the hippocampus, was assessed using the Barnes circular maze. Briefly, the maze is a 122 cm diameter white disc with 40 holes cut in the perimeter. A black plexiglass escape tunnel is attached underneath the table beneath one of the holes. In the test the mouse is motivated to escape the open, brightly lit maze that is associated with aversive noise from a buzzer. The Barnes maze is used in both spatial and cued versions, the cued version being a hippocampal-independent control. For the spatial version of the test the escape tunnel is always located under the same hole. To locate the hole in this test, the mouse needs to remember and use the relationships between distal cues in the room where the experiments are conducted. In the cued version of the test, a cue (a painted can 23 cm high) is placed directly behind the escape tunnel hole and the position of the escape tunnel is varied randomly each say. For both versions of the test the approach used in these experiments has followed that described previously (Bach et al 1995). Twenty-four hours before the first day of testing, the animals were submitted to a training session. Each test commenced by placing the animals in the center of the maze and covering them with a black container. After 30 to 50 s of habituation, 80 dB of white noise was produced and 10 s later the container was removed and the animal was allowed to explore the maze. The session ended when either the mouse entered the escape tunnel or there was no result after 4 min exploration time. As soon as the mouse found the hole, the noise was turned of and the animal was allowed to rest in the darkened escape tunnel. Variables recorded for each mouse were latency (time to find the escape tunnel), number of errors (searches of any hole without the tunnel underneath it), and the order of holes searched.

Figure 3:
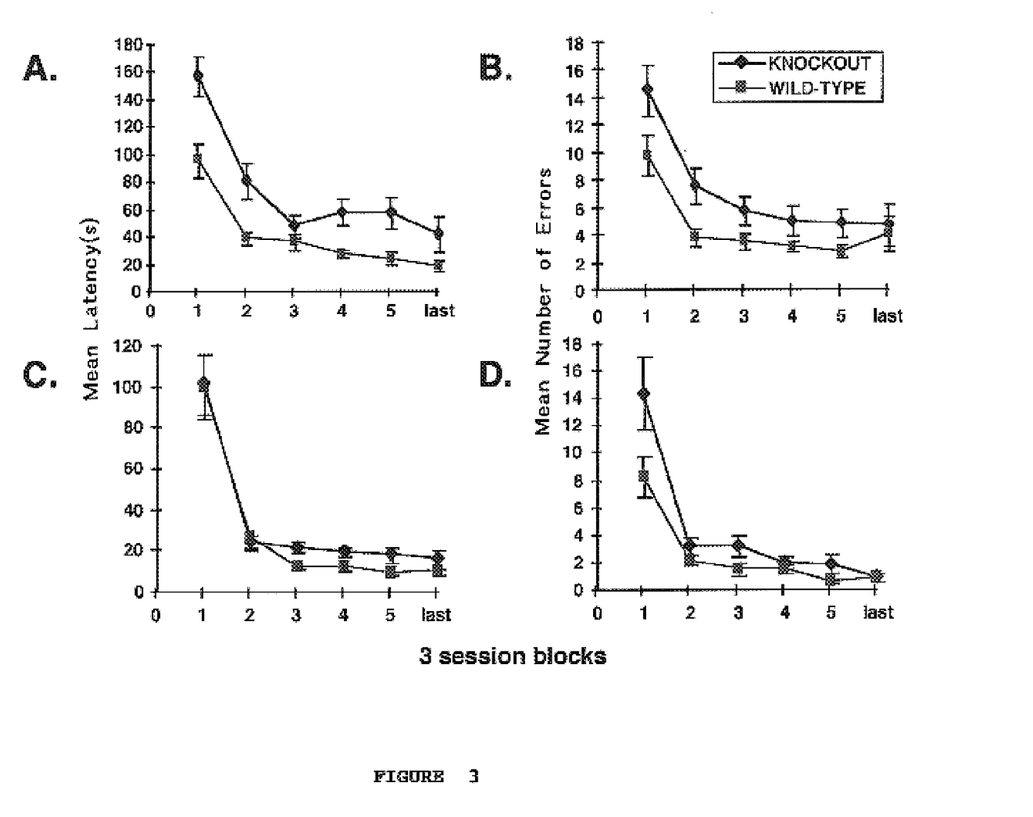
FIGS. 3A–D shows the Barnes circular maze test of wild-type and Dtk knockout mice: spatial and cued versions. A,B: spatial version. Data from 2 groups of males and 2 groups of females have been pooled and are presented as mean latency (A) and mean number of errors (B) for successive blocks of 3 sessions and the last session. C,D: cued version. Mean latency (C) and mean number of errors (D) with data pooled from 1 group of males and 2 groups of females. Values represent group means+/−SEM.

Seven groups of mice (4 male and 3 female) containing approximately equal numbers of wild-type and knockout mice have been tested in the spatial version and 3 groups (2 female and 1 male) have been tested in the cued version of the Barnes maze. Together these are representative of 15 litters of knockout mice (53 knockout mice in total), that have been reared under identical conditions to the wild-type. Results from a typical experiment are shown in FIG. 3.

The data show a significant difference in spatial learning between the wild-type and Dtk knockout mice, with Knockout mice consistently making more errors and taking a longer period of time to find the escape tunnel (latency). This has been a reproducible finding in all groups of animals studied, and both in males and females. A repeated measures analysis of variance with a Poisson error structure was used to investigate the difference in the numbers of errors made by the two types of mice over time and demonstrated a difference in the average number of errors between the wild-type and Dtk knockout mice (p=0.002). A multiplicative hazards model for censored data with multiple outcomes for each subject was used to investigate whether there was a difference between the groups in the time taken to find the escape route. There was a significant session by type-of-mouse interaction (p=0.005) demonstrating that the pattern of latency was different for the wild-type and Dtk knockout mice. For the cued version of the test there was no significant difference in latency between the two types of mice, but Dtk knockout mice made significantly more errors than wild-type (p=0.04), although this difference is not as dramatic as in the spatial version (FIG. 3). From these results then, the knockout mice demonstrate a defect in spatial learning and memory, although the results from the cued version do not rule out other effects such as differing anxiety levels in the two types of mice.

Behavioural Analysis: Conditioned Fear Paradigm

As behavioural studies of Dtk knockout mice in the Barnes circular maze indicated a defect in the hippocampal-dependent spatial task, we undertook further studies using another hippocampal-dependent task, fear conditioning. Pavlovian fear conditioning is a ubiquitous and simple form of learning that is exceptionally robust and rapidly acquired (Maren, 1996). Animals learn to fear a previously neutral stimulus (conditioned stimulus (CS)) because of its association with an aversive stimulus (unconditioned stimulus (US)), such as a foot shock. Conditioned animals tend to respond to the CS, by freezing. In this paradigm, freezing responses can be triggered by two different types of CS, tone and context, each of which requires distinct neuroanatomical substrates (Kim, et al 1992; Phillips, et al 1992). Cued conditioning, in which the CS is a tone, is dependent on the amygdala, and contextual conditioning, where the CS is a novel environment is dependent on both the hippocampus and amygdala. We evaluated both context memory, a hippocampus and amygdala-dependent task, and cued, an amygdala-dependent task.

The fear conditioning experiments were performed as described (Bourtchuladze, 1994). On the training day each mouse was placed in the conditioning chamber (Operant Mouse Chamber, Med Associates) and allowed to freely explore for 2 min. The chamber consisted of two transparent walls, two metal walls, a transparent plexiglass ceiling and a metal grid floor. After the 2 min habituation, the CS, a 80 dB, 2800 Hz white noise tone, was presented for 20 s. The last 2 seconds of CS were paired with a US, a 0.7 mA continuous footshock. The mouse was left in the chamber for an additional 30 s. The experimental conditions were controlled by computer with Med-PC software (Med Associates). Conditioned behaviour was evaluated 24 h later (n=47; 15 female and 11 male wild-type; 15 female and 6 male Dtk knockout) in one single trial by manually scoring the freezing behaviour, which was defined as complete lack of movement in intervals of at least 5 s, with the exception of respiration. Context conditioning (context-shock association) was assessed for 5 min in the chamber where the animals had been trained. The cued conditioning (tune-shock association) was assessed 2 h later by presenting the tone in a novel context. For this particular purpose, we used the rat operant chamber (Med Associates), the walls and floor of which were covered with paper and treated with a novel scent (air freshener). Animals were placed in the rat chamber and allowed to freely explore it for 3 min. A 3 min continuous tone (80 dB) was then presented, during which time freezing was manually recorded.

Figure 4:
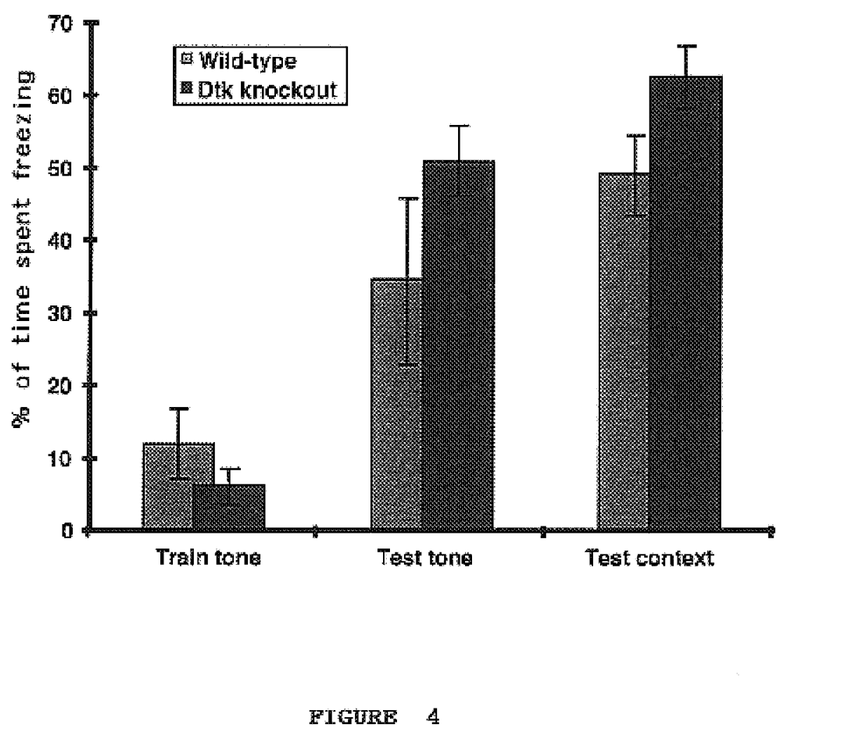
FIG. 4 shows the fear conditioning test of wild-type and Dtk knockout mice: cued and contextual versions. Percentage of time spent freezing to tone during training and to tone and context during testing, by wild-type and Dtk knockout mice. Values represent group means+/−SEM.

The results for contextual and cued fear conditioning 24 h after training are shown in FIG. 4 Both wild-type and Dtk knockout mice appeared to learn both tasks, judging from the increase in freezing noted during the respective tests compared to training. There was no significant difference between wild-type and Dtk knockout mice in the cued test (ANOVA; F[1,38]=0.61, p=0.4), but the knockout mice showed significantly more freezing than wild-type in the contextual test (F[1,50]=13.0, p=0.0007). In contrast to the results obtained using the Barnes maze, these data are not consistent with the hypothesis of a hippocampal defect in the Dtk knockout mice. On the other hand, it is possible that the mutant animals were more reactive to the stressful experience, which might mask a potential hippocampal defect. Mice expressing a $Ca^{2+}$-independent mutant of the $Ca^{2+}$/calmodulin-dependent protein kinase II have also been shown to exhibit a deficit in spatial navigation while satisfactorily accomplishing a contextual fear conditioning task (Bach, et al 1953), suggesting that spatial and contextual memory, although both being hippocampal-dependent, may be mediated by different synaptic mechanisms. It appears that the Dtk knockout mice exhibit a behavioural phenotype which involves a, hippocampal-dependent component.

Electrophysiological Analysis of Dtk Knockout Mice

Figure 5:
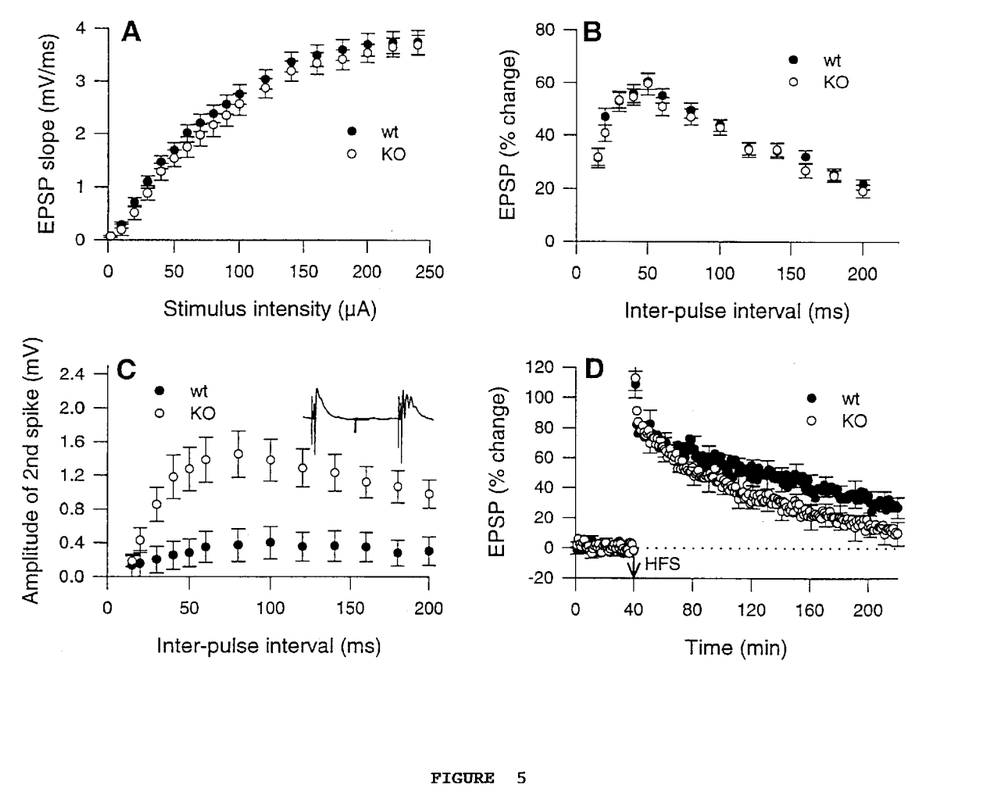
FIGS. 5A–D shows electrophysiological analysis of synaptic transmission and plasticity in the hippocampus of wild-type (wt) and Dtk knockout (KO) mice. A; input-output curve relating stimulation intensity to field excitatory post-synaptic potential (EPSP) slope; a measure of basal synaptic efficacy. B: facilitation of synaptic efficacy (measured as percentage change in EPSP slope) by delivering paired stimuli at various intervals; a measure of short-term plasticity C: paired-pulse facilitation of the population spike; a measure of recurrent inhibition. Inset: representative trace for Dtk knockout showing multiple spikes in response to second stimulus (scale: 10 ms, 1 mV). D: decaying form of LTP following single high-frequency tetanus (100 Hz, 1 s, indicated by arrow) Values for panels A–D represent means of measurements of up to 12 mice+/−SEM.

On the basis of the results from the Barnes circular maze, the electrophysiological characteristics of synaptic transmission in the Dtk knockout mice, in particular induction of long-term potentiation (LTP) in the hippocampus, have been analysed. LTP is a lasting form of potentiation of synaptic efficacy, hypothesised as a model for memory (Bliss and Lomo, 1973) Wild-type and Dtk knockout mice were coded so that all experiments were performed blind. After a 1–2 week recovery period, animals were anaesthetised with halothane and decapitated. Hippocampal slices (400 μm) were prepared according to standard protocols (Kerr and Abraham, 1995). Once made, the slices were superfused with a standard oxygenated bathing medium and maintained at 32.5° C. Extracellular stimulating electrodes (50 μm wires) and recording electrodes (micropipettes filled with 2 M NaCl, 1–3 Mohm) were placed into the slices under visual and electrophysiological guidance to maximise the evoked field potentials. For each individual slice, the electrodes were placed to record Schaffer collateral/commissural evoked responses (Kerr and Abraham, 1995). Results of the electrophysiological characterisation are shown in FIG. 5.

There was no difference observed in basal synaptic efficacy (FIG. 5, panel A) or in EPSP slope change with paired-pulse stimulation (panel B) between the wild-type and Dtk knockout mice. However, paired-pulse facilitation of the population spike was markedly enhanced in Dtk knockout mice (panel C), possibly indicating decreased recurrent inhibition. In addition, multiple spikes appeared in response to the second stimulus of the pair panel C, inset), an effect restricted to the knockout mice. Perhaps most interesting was a statistically significant (p<0.06) observed impairment in the persistence of LTP in the knockout mice. This was evident as a more rapid decay of potentiation without alteration of the initial short-term potentiation. These results indicate an impairment of LTP in the Dtk knockout mice, which together with the defect in spatial learning and memory in the Barnes circular maze, point towards a role of Dtk in LTP and learning and memory.

Experiment 2

Altered Cell Survival in the Hippocampus of Dtk-targeted Mice

Introduction

To study the function of Dtk, mice containing a targeted mutation in the Dtk gene have been generated (see Experiment 1) with deletion of exons 3 to 11 encoding the extracellular ligand-binding domain. Dtk knockout mice are viable and fertile, but have an impaired performance on the Barnes circular maze, a test of hippocampal-dependent spatial learning. In addition there is an impairment in the long-term potentiation (LTP) in the CA1 region of the hippocampus, where Dtk is normally expressed. LTP is a long-lasting form of synaptic plasticity which is the currently favoured molecular model for memory formation. These data support a role for Dtk in hippocampal-dependent learning and memory, either through a signalling contribution to LTP induction and maintenance, or through trophic support of neurons in the hippocampus. This experiment investigated the trophic support hypothesis.

Materials and Methods

Preparation of Bran Sections

Male wild-type and Dtk knockout mice (3 of each) at 9 weeks age were sacrificed by cervical dislocation. Brains were collected and snap frozen in isopentane on dry ice. Coronal 25 μm cryostat sections were thaw mounted onto poly-L-lysine coated slides, allowed to dry and stored at −80° C. For each mouse 36 sections were taken at 100 μm intervals throughout the extent of the hippocampus for analysis by TUNEL (terminal transferase-mediated dUTP nick end labelling). Adjacent sections were collected for staining with cresyl violet to outline the cellular architecture of the hippocampus.

TUNEL Staining

Sections for TUNEL staining were fixed for 10 min in 4% paraformaldehyde and washed in phosphate-buffered saline containing 0.2% Triton X-100 (PBS-T). Endogenous peroxides were inactivated by treatment with 1% $H_2O_2$ in methanol for 7 min, and slides were washed in PBS-T. Positive control sections were treated with 0.1 μl Dnase I (Boehringer Mannheim) in 20 mM iris HCl pH 8.3, 50 mM KCl, 2.5 mM $MgCl_2$, 100 μg/ml bovine serum albumin, for 30 min at 37° C. and washed in PBS-T. All sections were preincubated in TdT buffer (Life Technologies) for 20 min at room temperature, before biotin labelling of DNA ends with 0.15 U/μl terminal transferase (Life Technologies) and 4 μM biotin-14-dATP in TdT buffer for 4 h at 37° C. Terminal transferase was omitted from negative control slides. Slides were washed for 20 min in 2×SSC (0.3 M NaCl, 30 mM sodium citrate pH 7.0) and in PBS-T, then blocked for 12 min in 2% bovine serum albumin in PBS-T. After washing in PBS-T, sections were incubated in Extravidin Peroxidase (Sigma) at 1:100 in PBS-T for 2 h at room temperature. Slides were washed in PBS-T, and stained with diaminobenzidine (DAB, 0.05% in 0.1 M phosphate buffer, 0.01% $H_2O_2$). After a final wash in PBS-T, sections were dehydrated and coverslipped with histomount.

Cell Counts

Figure 6:
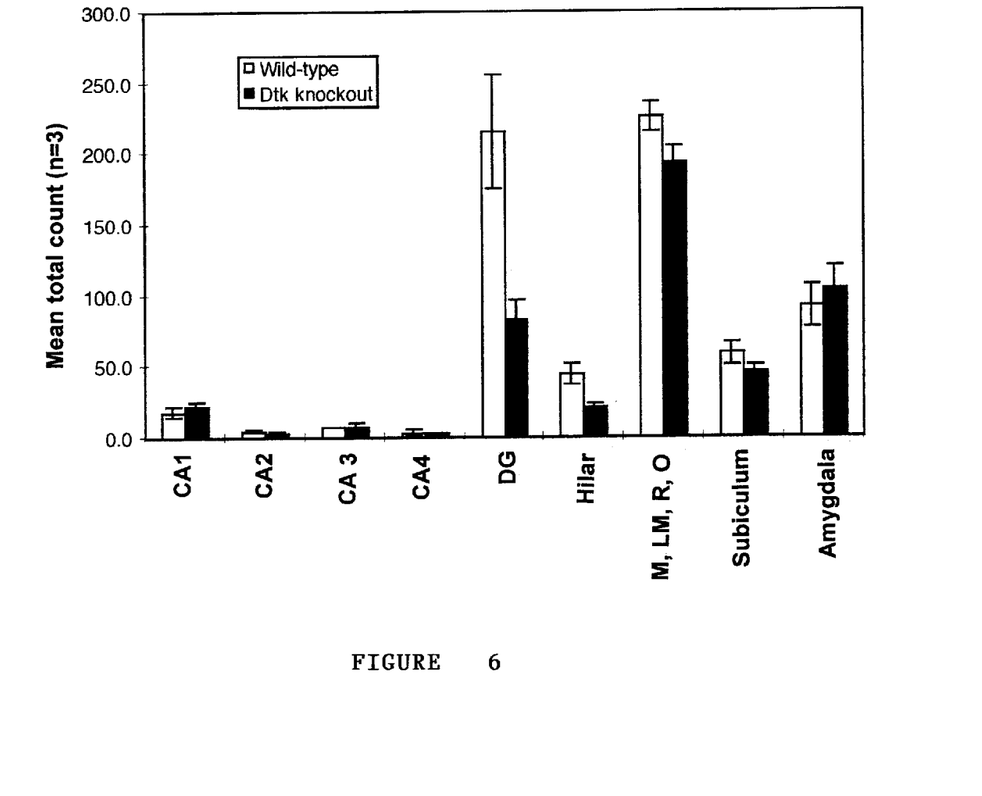
FIG. 6 shows cell death in wild-type vs Dtk knockout brain by TUNEL. Brains from 9 week old wild-type and Dtk knockout mice (3 of each) were snap frozen, and 25 $\mu$m coronal cryosections were taken at 100 $\mu$m intervals through the region containing the hippocampus (36 sections/mouse). TUNEL-positive cells were counted in the indicated regions and total counts were calculated for each mouse. Mean total counts are shown +/−SEM. Abbrevations: DG—dentate gyrus; LM—lacunosum-molecular layer; M—molecular layer; O—oriens layer; R—radiatum layer.

Slides of TUNEL-stained sections were independently coded and randomised to eliminate bias from cell counting procedures. TUNEL-positive cells were counted in different regions of the hippocampus, the subiculum and amygdala, and total counts for all sections for each mouse were calculated. Statistical comparison of mean total counts for wild-type and Dtk knockout mice was carried out by two-tailed Student's e-test Results and Discussion If Dtk acts as a survival factor for neurons then increased cell death as a consequence of mutating the Dtk gene could be responsible for the observed deficits in LTP and spatial learning. To test this hypothesis, coronal sections from wild-type and Dtk knockout mouse brains were TUNEL stained to detect DNA fragmentation. TUNEL-positive cells were counted in different regions of the hippocampus and in the amygdala and subiculum (FIG. 6).

Figure 7:
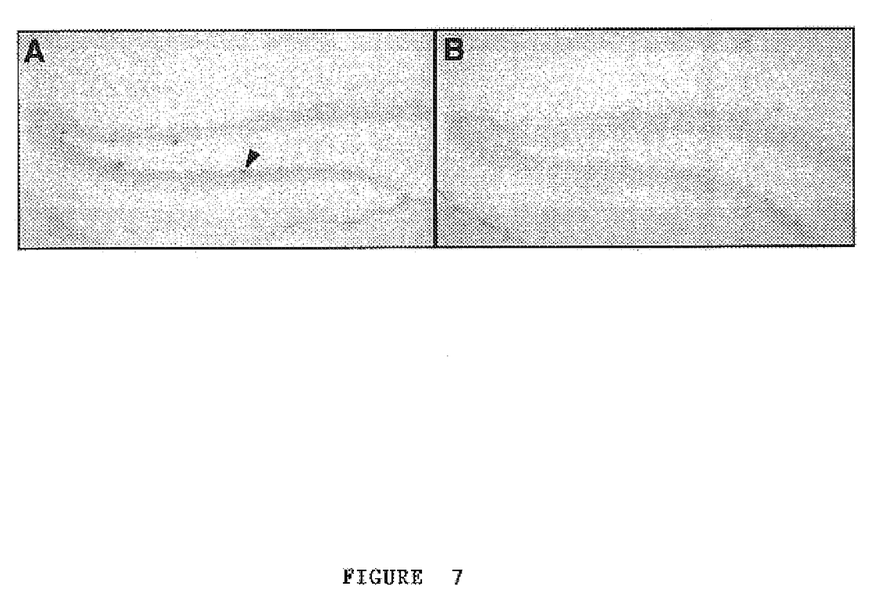

In area CA1 of the hippocampus, where Dtk is primarily expressed, there was no observed difference in cell death between wild-type and Dtk knockout mice. Similar levels of cell death between wild-type and Dtk knockout animals were also seen in the amygdala and subiculum, in hippocampal areas CA2, CA3 and CA4, and in the molecular, lacunosum-molecular, radiatum and oriens layers of the hippocampus. However, the Dtk knockout mice exhibited a 2–3 fold decrease in TUNEL-positive cell counts in the hilar region and granule cell layer of the dentate gyrus (p<0.05). This result is somewhat paradoxical, as Dtk is not normally expressed in this region and the trophic support hypothesis would have predicted an increase in cell death in the absence of Dtk. The majority of TUNEL-positive cells in the dentate gyrus lie on the granule cell layer-hilar border (FIG. 7), which has been identified as a region of neurogenesis in adult rodents (Bayer et al (1982); Crespo et al (1996)). This leads to speculation that the alteration in cell death in this region may be mirrored by a change in neurogenesis.

It is not known whether the observed decrease in cell death in the dentate granule cell layer and hilar region is linked to the behavioural phenotype of the Dtk knockout mice, or, for that matter, if it is physiologically significant. However, the observation that there is no increase in apoptosis in area CA1 suggests that a loss of trophic support for CA1 pyramidal neurons is not primarily responsible for the observed deficits in LTP and spatial learning in the Dtk knockout animals.

Industrial Application

The invention has application in the modulation of LTP, learning, memory and/or anxiety states. These applications involve influencing the activity of the Dtk receptor tyrosine kinase in the brain.

While the primary application of the invention will be in terms of increasing the activity of Dtk receptor tyrosine kinase in the prophylaxis or therapy of LTP, learning, memory and/or anxiety disorders, the finding of the invention also gives rise to the possibility of decreasing the activity of the Dtk receptor tyrosine kinase where this could be of benefit. Such a decrease in activity can be effected through the use of inhibitory ligands which bind to the extracellular binding domain of Dtk receptor tyrosine kinase but which are incapable of initiating signal transduction from the kinase domain. Similarly, the extracellular binding domain of Dtk receptor tyrosine kinase in a soluble form can itself be used. The extracellular binding domain will have the capacity to reduce the amount of ligand available to bind to Dtk receptor tyrosine kinase and initiate signal transduction.

It will however be appreciated that the principal approach will be to increase Dtk receptor tyrosine kinase activity in the brain for the purpose of prophylaxis or therapy of LTP, learning, memory and/or anxiety disorders. Such disorders include all neurodegenerative diseases, with Alzheimer's Disease and ADD being specific examples.

To the extent that learning and memory disorders could arise from loss of neurons through degenerative processes involving cell death or apoptosis, the invention may also have application in neuroprotection to prevent or ameliorate neuronal cell loss. Specifically, indications are that the Dtk receptor is involved in providing an anti-apoptotic signal within the brain.

The increase in activity of Dtk receptor tyrosine kinase can be achieved in a number of ways. These include direct administration of stimulatory ligands. Such ligands can be any ligand which is capable of binding to the extracellular binding domain of Dtk receptor tyrosine kinase and initiating signal transduction from the kinase domain.

One stimulatory ligand suitable for use in the invention is the ligand known as Gas6. This ligand is described in U.S. Pat. No. 5,538,861 to Schneider et al. Functionally equivalent analogs to Gas6 can also be used.

Another approach to increasing the activity of Dtk receptor tyrosine kinase is through the administration of Gas6 agonists. These agonists are compounds which, when administered to a patient act to amplify the effect of Gas6 on signal transduction from the kinase domain of Dtk receptor tyrosine kinase. This can be through effecting an increase in the production of Gas6 within the patient or inhibition of Gas6 antagonists.

Another possibility is administration of a replicable vehicle encoding Gas6 to the patient. Such a vehicle (which may be a modified cell line or virus which expresses Gas6 within the patient) could have application in increasing the concentration of Gas6 within the patient for a prolonged period. Such a vehicle could well form part of a brain implant.

In addition to Gas6 itself, the use of analogs of Gas6 or functionally equivalent ligands of Gas6 is contemplated.

As used herein "analog" means a protein which is a variant of Gas6 through insertion, deletion or substitute of one or more amino acids but which retains at least substantial functional equivalency.

A protein is a functional equivalent of another protein for a specific function if the equivalent protein is immunologically cross-reactive with, and has at least substantially the same function as, the original protein. The equivalent can be, for example, a fragment of the protein, a fusion of the protein with another protein or carrier, or a fusion of a fragment with additional amino acids. For example, it is possible to conservatively substitute amino acids in a sequence with equivalent amino acids using conventional techniques.

Functional equivalency of Gas6 analogs can also be readily screened for by reference to the ability of the analog to both bind to and activate Dtk receptor tyrosine kinase.

In addition to Gas6 and its analogs, other stimulatory ligands can be identified by a screening protocol which, for example, utilises the expression of Dtk receptor tyrosine kinase in an appropriate cell line and measures the Dtk receptor-mediated signal transduction via the kinase domain evoked by stimulatory ligands. Further, classical "rind and bind" ligand-binding experiments can also be utilised. Here, whole brain or specific brain regions would be homogenised and specific-binding of compounds to Dtk receptor tyrosine kinase characterised. This technique allows further characterisation of its specificity and affinity (potency) of the compound for the Dtk receptor tyrosine kinase complex.

For use in the methods of the invention, the active compound (whether it be Gas6, a Gas6 analog or another functionally equivalent ligand) will be formulated as a medicament. The details of the formulation will ultimately depend upon the therapeutic effect to be induced and the selected route of administration. However, it will be usual for the active compound to be combined with a suitable carrier, vehicle or diluent.

To be effective in the methods of the invention, a variety of administration routes can be used. Examples include intracerebroventricularly (ICF) and intraventricular administration involving neurosurgical insertion of a ventricular cannular with an abdominal pump and reservoir.

Dosage rates will also be formulation- and therapy-dependent. However, by way of example, the recommended dosage rate of Gas6 for injection would be in the range of 1–100 $\mu$g per kg.

In addition to the methods of direct therapy or prophylaxis, the invention also provides methods for identifying compounds having utility in either the enhancement of LTP, learning and/or memory capability or in the reduction or amelioration of an anxiety state. Such methods involve the use of a non-human vertebrate animal which has been genetically modified so that expression of Dtk receptor tyrosine kinase in the brain of the animal is reduced if not eliminated. By way of example, the genetically modified mouse which is a Dtk receptor tyrosine kinase null mutant can be employed.

These methods will employ such an animal as a screen in relation to test compounds. The test or candidate compounds are administered to the animal and the effect of the compounds upon LTP, learning/memory/anxiety measured. The resulting measurement is then compared against the predetermined base line measurement for the animal in the absence of the compound in order to identify those test compounds which either enhance LTP, learning and/or memory or reduce anxiety.

Those persons skilled in the art will appreciate that the above description is provided by way of example only and that modifications can be made without departing from the scope of the invention.

References

Bach, M. E., Hawkins, R. D., et al (1995). "Impairment of spatial but not contextual memory in CaMKII mutant mice with a selective loss of hippocampal LTP in the range of the theta frequency." *Cell* 81(6): 905–15.

Bayer, S. A, Yackel, J. W. and Puri, P. S. *Science* 216, 890–2 (1982).

Bliss, T. V., and Lomo, T. (1973). "Long-lasting potentiation of synaptic transmission in the dentate area of the anaesthetised rabbit following stimulation of the perforant path." *Journal of Physiology* 232(2): 31–56.

Bourtchuladze, R., Frenguelli, B., et al (1994). "Deficient long-term memory in mice with a targeted mutation of the cAMP-responsive element-binding protein." *Cell* 79(1): 59–68.

Crespo, D., Stanfield, B. B. and Cowan, W. M. Experimental Brain Research 62, 541–8 (1986).

Crosier, K. E. et al, *Growth Factors* 11, 137–44 (1994).

Crosier, K. E. and Crosier, P. S. *Pathology* 29, 131–135 (1997).

Crosier, P. S., Freeman, S. A., Orlic, D., Bodine, D. M. and Crosier, K. E. *Experimental Haematology* 24, 18–23 (1996).

Crosier, P. S., Lewis, P. M., et at. (1994). "Isolation of a receptor tyrosine kinase (DTK) from embryonic stem cell; structure, genetic mapping and analysis of expression." *Growth Factors* 11(2): 125–36.

Faust, M., et al. *Oncogene* 7, 1287–93 (1992).

Graham, D. K., Dawson, T. L., Mullaney, D. L., Snodgrass, H. R. and Earp, H. S. *Cell Growth and Differentiation* 5, 647–57 (1994).

Graham, D. K. et al *Oncogene* 10, 2349–2359 (1995).

Hogan, B., Costantini, F., et al (1986). *Manipulating the mouse embryo. A laboratory manual* Plainview, N.Y., Cold Spring Harbour Laboratory Press.

Jia, R. and Hanafusa, H. *Journal of Biological Chemistry* 269, 1839–44 (1994).

Kerr, D. S. and Abraham, W. C. (1995). "Cooperative interactions among afferents govern the induction of homosynaptic long-term depression in the hippocampus." *Proceedings of the National Academy of Sciences of the United States of America* 92(25): 11637–41.

Kim, J. J. and Fanselow, M. S. (1992). "Modality-specific retrograde amnesia of fear." *Science* 256 (5057): 675–7.

Lai, C., Gore, M. and Lemke, G. *Oncogene* 9, 2567–78 (1994).

Maren, S. (1996). "Synaptic transmission and plasticity in the amygdala. An emerging physiology of fear conditioning circuits." *Mol. Neurobiol* 13(1): 1022.

McHugh, T. J., Blum, K. I., et al (1996). "Impaired hippocampal representation of space in CA1-specific NMDAR1 knockout mice." *Cell* 87(7):1339–49.

Neubauer, A., et al *Blood* 84, 1931–41 (1994).

Phillips, R. G. and LeDoux, J. E. (1992). "Differential contribution of amygdala and hippocampus to cued and contextual fear conditioning." *Behavioural Neuroscience* 106(2): 274–85.

Schulz, N. T., Paulhiac, C. I., Lee, L. and Zhou, R. *Molecular Brain Research* 28, 273–80 (1995).

Szabo, P. and Mann, J. R. (1994). "Expression and methylation of imprinted genes during in vitro differentiation of mouse parthenogentic and androgentic embryonic stem cell lines." *Development* 120(6): 1651–60.

Thomas, K. R. and Capecchi, M. R. (1987). "Site-directed mutagenesis by gene targeting in mouse embryo-derived stem cells." *Cell* 61(3): 503–12.

Tsien, J. Z., Huerta, P. T., et al. (1996). "The essential role of hippocampal CA1 NMDA receptor-dependent synaptic plasticity in spatial memory." *Cell* 87(7); 1327–38.

Tybulewicz, V. L., Crawford, C. E., et al (1991). "Neonatal lethality and lymphopenia in mice with a homozygous disruption of the c-abl proto-oncogene." *Cell* 65(7): 1153–63.

What is claimed is:

1. A transgenic knockout mouse having a homozygous disruption of a Dtk tyrosine kinase gene and which has no expression of Dtk receptor tyrosine kinase in the brain of said knockout mouse relative to a wild-type mouse, said knockout mouse exhibiting a defect in spatial learning and/or memory, and/or an increased anxiety response, and/or an impairment of long-term potentiation (LTP).

2. A transgenic knockout mouse having a homozygous disruption of a Dtk tyrosine kinase gene so that the expression of Dtk receptor tyrosine kinase is eliminated in the forebrain of said knockout mouse relative to the wild-type mouse, and said knockout mouse exhibiting a defect in spatial learning and/or memory, an increased anxiety response, and an impairment of long-term potentiation (LTP).

3. A method of identifying compounds which are capable of enhancing long-term potentiation (LTP), learning and/or memory capability which comprises:

establishing an LTP, learning and/or memory deficit baseline level for a transgenic knockout mouse having a homozygous disruption of a Dtk receptor tyrosine kinase and which has no expression of Dtk receptor tyrosine kinase in the brain of said knockout mouse relative to a wild-type mouse, and said knockout mouse exhibiting a defect in spatial learning and/or memory, and/or an increased anxiety response, and/or impairment LTP;

administering candidate compounds separately to said transgenic knockout mouse; and identifying those compounds which enhance LTP, learning and/or memory relative to the baseline.

4. A method of identifying compounds which are capable of reducing or ameliorating an anxiety state which comprises:

establishing an anxiety quotient baseline level for a transgenic knockout mouse having a homozygous disruption of a Dtk receptor tyrosine kinase gene and which has no expression of Dtk receptor tyrosine kinase in the brain of said knockout mouse relative to a wild-type mouse, and said knockout mouse exhibiting a defect in spatial learning and/or memory, and/or an increased anxiety response, and/or impairment of long-term potentiation (LTP);

administering candidate compounds separately to said transgenic knockout mouse; and identifying those compounds which reduce anxiety levels relative to said anxiety quotient baseline.

5. A method of identifying compounds which are capable of enhancing long-term potentiation (LIP), learning and/or memory capability which comprises:

establishing an LTP, learning and/or memory deficit baseline level for a transgenic knockout mouse of claim 2;

administering candidate compounds separately to said transgenic knockout mouse; and identifying those compounds which enhance LTP, learning and/or memory relative to the baseline.

6. A method of identifying compounds which are capable of producing or ameliorating an anxiety state which comprises:

establishing an anxiety quotient baseline level for a transgenic knockout mouse of claim 2;

administering candidate compounds separately to said transgenic knockout mouse; and identifying those compounds which reduce anxiety level relative to said anxiety quotient baseline.

* * * * *